US011324415B2

(12) United States Patent
Dietz

(10) Patent No.: US 11,324,415 B2
(45) Date of Patent: May 10, 2022

(54) CONDUCTIVITY COMPENSATION FACTOR FOR ASSESSING BIOELECTRIC MEASUREMENTS

(71) Applicant: Vine Medical LLC, Saint George, UT (US)

(72) Inventor: Phillip W. Dietz, Saint George, UT (US)

(73) Assignee: Vine Medical LLC, Saint George, UT (US)

( * ) Notice: Subject to any disclaimer, the term of this patent is extended or adjusted under 35 U.S.C. 154(b) by 171 days.

(21) Appl. No.: 16/660,613

(22) Filed: Oct. 22, 2019

(65) Prior Publication Data

US 2020/0121216 A1 Apr. 23, 2020

Related U.S. Application Data

(60) Provisional application No. 62/748,637, filed on Oct. 22, 2018.

(51) Int. Cl.

| | |
|---|---|
| ***A61B 5/0531*** | (2021.01) |
| ***G16H 70/20*** | (2018.01) |
| ***A61B 5/00*** | (2006.01) |

(52) U.S. Cl.
CPC .......... *A61B 5/0531* (2013.01); *A61B 5/7203* (2013.01); *A61B 5/742* (2013.01); *G16H 70/20* (2018.01)

(58) Field of Classification Search
CPC .......... A61B 2560/0223; A61B 5/0531; A61B 5/0532; A61B 5/053; A61B 5/0537; A61B 2562/04; A61B 2562/043; A61B 2562/046; A61B 5/0533; A61B 5/7203; A61B 5/7221; G16H 70/20; G06Q 50/24; G06F 19/32; G06F 19/324
See application file for complete search history.

(56) References Cited

U.S. PATENT DOCUMENTS 4,625,732 A 12/1986 Kasa et al.
5,540,235 A 7/1996 Wilson
6,934,581 B2 8/2005 Kanevsky
2003/0120170 A1* 6/2003 Zhu ...................... A61B 5/4869 600/547
2006/0212104 A1* 9/2006 Hindinger ............ A61H 39/002 607/150
2009/0036793 A1* 2/2009 Clark .................. A61B 5/0532 600/547
2012/0316457 A1* 12/2012 Meng .................. A61B 5/4854 600/548

(Continued)

FOREIGN PATENT DOCUMENTS

JP 2003126055 A * 5/2003

*Primary Examiner* — Sean P Dougherty
*Assistant Examiner* — Jonathan E. Cooper
(74) *Attorney, Agent, or Firm* — Terrence J. Edwards; TechLaw Ventures, PLLC

(57) ABSTRACT

Systems, methods, and devices for capturing and assessing bioelectric measurements. A method includes receiving a skin resistance measurement for a skin site of a user from an electrodermal sensor and determining a standard skin conductivity value. The method includes calculating a compensation factor for the user based at least in part on the skin resistance measurement and the standard skin conductivity value.

20 Claims, 9 Drawing Sheets

100
118
116
114
112
110
120
120
108
106
102
104

(56) References Cited

U.S. PATENT DOCUMENTS

2013/0261493 A1* 10/2013 Lin .................... A61B 5/0002 600/548
2015/0289820 A1 10/2015 Miller et al.
2016/0174869 A1* 6/2016 Park .................... A61B 5/0536 600/393
2017/0014043 A1* 1/2017 Mcdonnell ............. C23C 18/38
2017/0367614 A1* 12/2017 Zuckerman-Stark ....................... A61B 5/4824
2021/0153796 A1* 5/2021 De Weser ............ B60W 40/08

* cited by examiner

Figure 9:
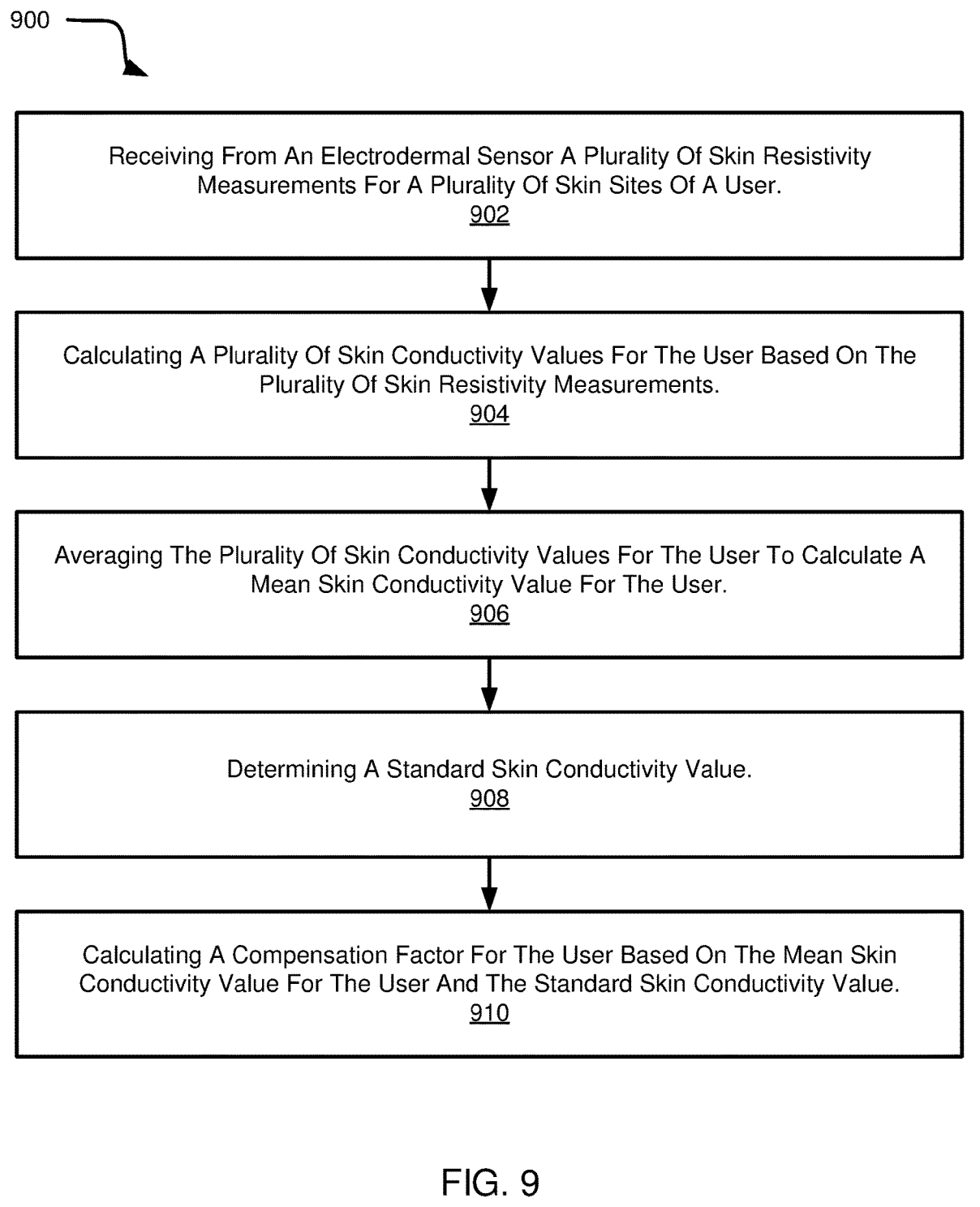

900

Receiving From An Electrodermal Sensor A Plurality Of Skin Resistivity Measurements For A Plurality Of Skin Sites Of A User.
902

Calculating A Plurality Of Skin Conductivity Values For The User Based On The Plurality Of Skin Resistivity Measurements.
904

Averaging The Plurality Of Skin Conductivity Values For The User To Calculate A Mean Skin Conductivity Value For The User.
906

Determining A Standard Skin Conductivity Value.
908

Calculating A Compensation Factor For The User Based On The Mean Skin Conductivity Value For The User And The Standard Skin Conductivity Value.
910

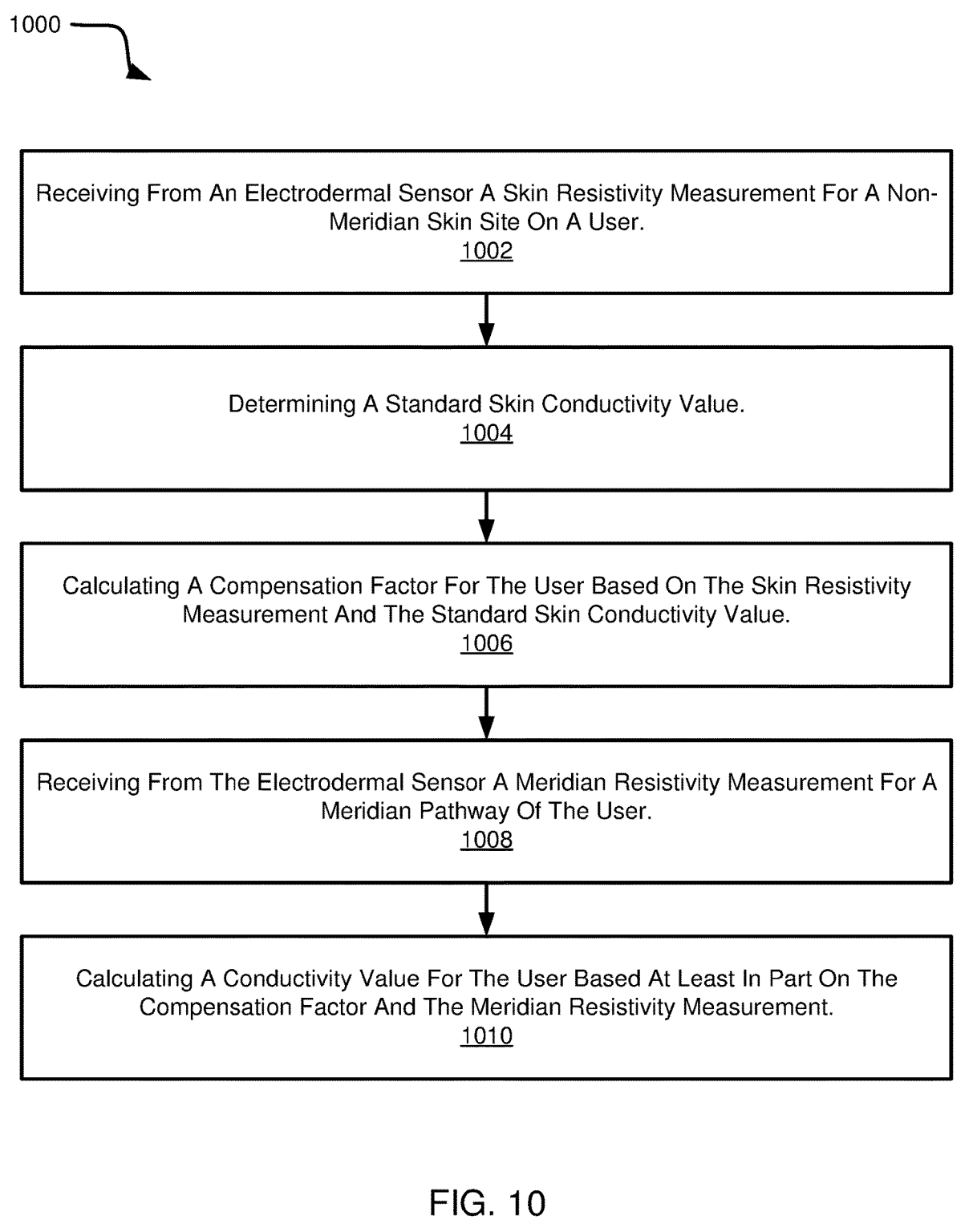

Receiving From An Electrodermal Sensor A Skin Resistivity Measurement For A Non-Meridian Skin Site On A User.
1002

Determining A Standard Skin Conductivity Value.
1004

Calculating A Compensation Factor For The User Based On The Skin Resistivity Measurement And The Standard Skin Conductivity Value.
1006

Receiving From The Electrodermal Sensor A Meridian Resistivity Measurement For A Meridian Pathway Of The User.
1008

Calculating A Conductivity Value For The User Based At Least In Part On The Compensation Factor And The Meridian Resistivity Measurement.
1010

FIG. 10

CONDUCTIVITY COMPENSATION FACTOR FOR ASSESSING BIOELECTRIC MEASUREMENTS

CROSS-REFERENCE TO RELATED APPLICATIONS

This application claims the benefit of U.S. Provisional Application No. 62/748,637, filed Oct. 22, 2018, titled, "METHODS, SYSTEMS, AND DEVICES FOR OBTAINING A CONDUCTIVITY COMPENSATION FACTOR FOR BIOELECTRIC MEASUREMENTS," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure is directed to bioelectric measurements and is particularly directed to conductivity compensation factors for bioelectric measurements.

BACKGROUND

The electrical conductance of body tissue can be measured and analyzed to gather information about a body's condition and to aid in diagnosing certain conditions. One form of measuring electrical conductance of body tissue is Electroacupuncture According to Voll (EAV). EAV and other electrical conductance diagnostic systems measure conductance levels at meridian points of the body. These electrical conductance diagnostic system are used by some health practitioners to gain additional insight into the body's compatibility with certain supplements or materials, whether certain pathogens or toxins reside in the body, dental conditions in the body, and more.

However, the conductivity of body tissue varies from person to person. Specifically, the conductivity of skin tissue can vary widely and can impact the readings gathered by an electrical conductance diagnostic system. The conductivity of skin tissue is dependent on a variety of factors, including whether the skin is moisturized, whether the skin is inflamed, whether the person suffers from a skin condition, and so forth. Further, there can be significant variance in skin conductivity even among samples of healthy and moisturized skin tissue. These differences in skin conductivity can lead to inaccurate measurements by electrical conductance diagnostic systems.

In light of the foregoing, disclosed herein are systems, methods, and devices for compensating for the unique skin conductivity of a person undergoing an electrical conductance test.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 9 illustrates a schematic flow chart diagram of a method for calculating a compensation factor for tissue conductivity;

FIG. 10 illustrates a schematic flow chart diagram of a method for calculating a conductivity value for a user.

DETAILED DESCRIPTION

Figure 1:
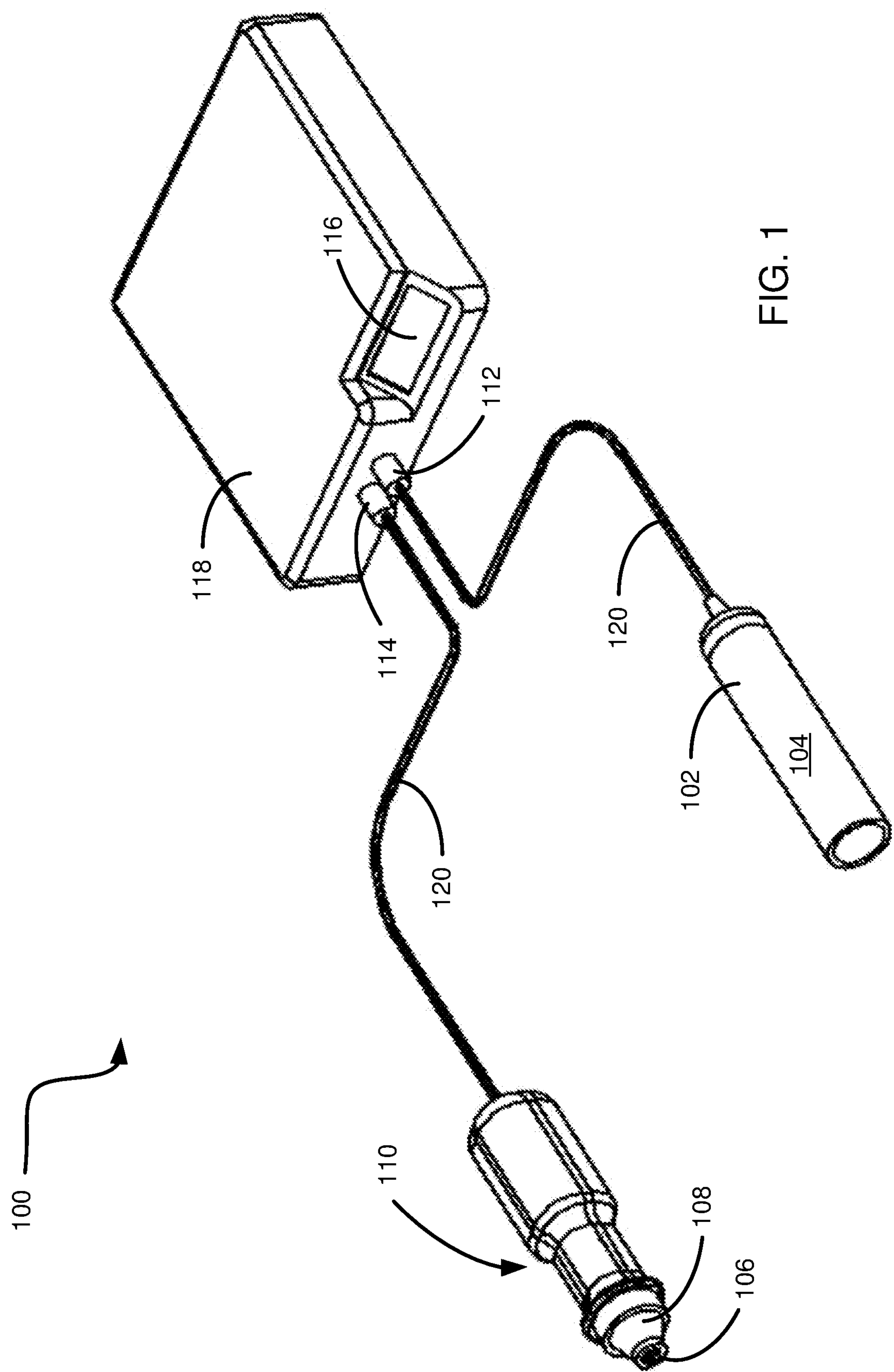
FIG. 1 illustrates an example of a bioelectric measurement system including an electrodermal sensor, a grounding device, and one or more processors in communication with the electrodermal sensor and the grounding device.

Disclosed herein are systems, methods, and devices for calculating and applying a compensation factor to bioelectric measurements. The compensation factor may be used in conjunction with an electrical conductance diagnostic system such as an Electroacupuncture According to Voll (EAV) or other electrodermal sensor system. The compensation factor is based on bioelectrical measurements of a user's skin that measure the overall conductivity of the user's skin.

An embodiment of the disclosure is a system for sensing the electrical conductance of a material such as body tissue. The system may sense the bio-conductivity of body tissue such as skin or some other tissue. An embodiment of the system includes an electrodermal sensor for contacting a user's skin and reading the electrical conductance of the user's skin. The electrodermal sensor may include one or more probe tips positioned on the electrodermal sensor to contact a site of the user's skin. In an embodiment, each of the one or more probe tips is independent and takes independent measurements of the user's skin.

The measurements taken by the system can be assessed for determining a skin resistance measurement and/or a meridian conductivity measurement for the user. The meridian conductivity measurement may include a meridian stress assessment for measuring energy associated with acupuncture meridians. The measurements can be used in multiple healthcare practices such as bio resonance therapy, bioenergy regulatory techniques, biocybernetics medicine, computerized electrodermal screening, computerized electrodermal stress analysis, electrodermal testing, limbic stress assessment, meridian energy analysis, point testing, and others.

However, the measurements taken by an electrodermal sensor can be inaccurate and ineffective if the user has nontypical skin conductivity. Many of the treatments and diagnoses determined based on electrodermal sensor readings are based on typical skin conductivity and cannot be effectively applied to users with nontypical skin conductivity. In light of this deficiency, disclosed herein are systems, methods, and devices for calculating and implementing a compensation factor for skin resistance measurements. The compensation factor may be applied to meridian conductivity measurements to calculate a conductivity value for the user.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Electroacupuncture According to Voll (EAV) devices can be deployed to measure conductance levels at meridian points in a body. An EAV device is a sensitive ohm meter for measuring resistance in the body. The resistance of a material, tissue, meridian pathway, and so forth can be assessed to calculate the conductivity of the material, tissue, or meridian pathway. A material with a lower resistance measurement will have a higher conductivity.

To detect resistance, an ohm meter (such as an EAV device) applies a small direct current flow through a material. Resistance measures the relative difficulty for current to flow through the material. Electrical conductors allow current to flow easily and have a correspondingly low resistance. Electrical insulators restrict current flow through and have a correspondingly high resistance. Ohm's Law applies to materials with a proportional relationship between voltage, current, and resistance according to:

$$V=RI$$

where V is voltage (measured in volts), I is current (measured in amps) and R is resistance (measured in ohms). Conductivity is the reciprocal of resistivity, expressed mathematically as 1/R and indicates a degree to which a specified material conducts electricity.

Human tissue generally has a resistance of about 98,000 Ohms between the tissue and ground. Meridian points have a general resistance of about 5,000 Ohms between the meridian point and ground. This means that meridian points throughout the human body are about twenty times more conductive than the tissue surrounding the points. This large differential in conductivity makes it possible to locate meridian points and to be very consistent in verifying the points with an EAV device.

Now referring to the figures, FIG. 1 illustrates a perspective view of a bioelectric measurement system 100. The bioelectric measurement system includes an electrodermal sensor 110, grounding device 102, and a processor 118 in electrical communication with the electrodermal sensor 110 and the grounding device 102.

The grounding device 102 may include a handheld mass to be held by a user undergoing measurements by the bioelectric measurement system 100. The grounding device 102 may include a brass road or other suitable material for grounding the user. The grounding device 102 includes a grounding surface 104 disposed around an exterior of the grounding device 102. The grounding surface 104 may include textures or grounding segments to improve the grounding capabilities of the grounding device 102. In an embodiment, the grounding surface 104 includes a plurality of grounding segments and each of the plurality of grounding segments may be included or excluded independently in the bioelectrical measurement. In an embodiment, the processor 118 determines which one or more of the grounding segments are included to reach the most accurate conductivity reading.

In an embodiment, the grounding device 102 is a small electrode similar to those used in conjunction with an electrocardiogram (EKG). The grounding device 102 may be any suitable size or shape and may be formed in an ergonomic size and shape that is easy for a user hold in the palm of the user's hand.

In an embodiment, the grounding device 102 is connected to a base and sits on a flat surface. This allows a test subject to rest a hand on the flat surface while gripping the grounding device 102. The grounding device 102 may be arched, domed, flat, or curved to aid in the connection between the body of the test subject and the grounding device 102. The grounding device 102 may be segmented such that each segment can individually be included or excluded from conductance calculations. In an embodiment, the grounding device 102 includes access to a moistening agent that is located within the grounding device 102, is attached to the grounding device 102, or is associated with the grounding device 102.

In an embodiment, the grounding surface 104 is a sufficiently large size to provide ample grounding to take consistent and accurate measurements. In an embodiment, the grounding surface 104 is at least five square inches to establish some margin of extra grounding area to maintain ground saturation and a constant ground resistance measurement even if the moisture on the hands evaporates and causes the need for the contacting area to enlarge to maintain ground saturation.

Meridian points in the body are located underneath skin tissue. This increases the difficult of measuring resistance associated with the meridian point because the skin tissue can become dry and act as an insulator. To minimize this insulating effect, a mist of liquid may be sprayed on the hand that grips the grounding device 102 to increase the conductivity of the skin tissue that is gripping grounding device 102.

The electrodermal sensor 110 is configured to measure the resistance of skin, meridian pathway in a body, or other materials or tissues. The readings taken by the electrodermal sensor 110 can be assessed to calculate the conductivity of the skin, meridian pathway in the body, or other materials or tissues. The electrodermal sensor may include a sensor hood 108 and one or more probe tips 106 disposed at a distal end of the electrodermal sensor 110 with respect to the electrical connection with the processor 118. The one or more probe tips 106 may be placed against the skin of a user to enable the electrodermal sensor 110 to measure the resistance of the skin or meridian pathway in the user. In an embodiment, the electrodermal sensor 110 takes a measurement when the one or more probe tips 106 are pressed against tissue. The one or more probe tips 106 may be constructed of any suitably electrically conductive material such as copper, silver, gold, aluminum, zinc, nickel, brass, iron, steel, or other material known to those skilled in the art.

In an embodiment, the probe tip 106 is a single probe tip 106. In an alternative embodiment, the probe tip 106 includes a plurality of individual probe tips. In an embodiment, each of a plurality of probe tips 106 can take an independent bioelectrical measurement. Probe tips 106 may further be divided into one or more primary probe tips located at the center and secondary probe tips 106 that are positioned around the one or more primary probe tips located at the center. The probe tip 106 may be textured to help penetrate the insulation layer or cornified layer of the tissue without puncturing it. In another embodiment, grounding pads may be integrated with the sensor hood 108.

The processor 118 may include one or more processors configurable to execute instructions stored in non-transitory computer readable storage media. The bioelectric measurement system 100 may include memory stored locally therein and accessible by the processor 118. The processor 118 is in electrical communication with the electrodermal sensor 110, the grounding device 102, and a display 116. In the illustration shown in FIG. 1, the processor 118 is in electrical communication with the electrodermal sensor 110 by way of a sensor connection point 114 and is in electrical communication with the grounding device 102 by way of the grounding connection point 112. The electrical communication between the processor 118 and the electrodermal sensor 110 and/or the grounding device 102 can be facilitated by an electrically conductive cable 120. Alternatively, the electrical communication may be made wirelessly through a wireless network such as a wireless personal area network (WPAN), a wireless local area network (WLAN), and so forth. The electrically conductive cable 120 may further be connected to a power source such that the electrodermal sensor 110 and/or the grounding device 102 are powered by way of an external power source.

Even with adding moisture to the contacting surfaces and the use of a textured surface, the conductivity of tissue from person to person may not be the same. For example, an adult female subject was tested having chronic skin issues. The subject was relatively healthy in all other areas. At the time, the machine that tested the subject considered all test measurements between a score of 45 and 55 to be healthy and in balance. Any measurement below a score of 45 entered an unbalanced area of lower conductivity and was considered to be a chronic issue. Any measurement above a score of 55 was out of balance and could be inflamed tissue with higher than normal conductivity and projected a possible acute issue. As the subject was tested all of her systems had measurements or scores of about 65 with the exception of her skin, which was measurement in balance with a measurement around 50. According to the measurements and without compensation factor, her skin was healthy and all of her other systems were having short term acute health issues. Thus, the methods, systems, and devices of the disclosure utilize the overall skin composition or general conductivity from patient to patient. The female subject's skin was hydrated and more conductive than the average person upon which the system had been calibrated.

The methods, systems, and devices of the disclosure for testing subjects apply a compensation factor to accommodate unique skin conductivity of subjects. For example, in the above example, if the female subject's scores or measurements were all lowered or compensated with a factor, for example by about 15 points, then all of her systems would have been measured at a balanced and healthy 50 and her skin would have had a measurement of 35 indicating that it would have had a chronic issue and the test results would have been accurate.

Accuracy in conductivity measurements and assessments is paramount in ensuring proper treatment or diagnosis. Other methods to increase accuracy is to decrease the insulating effect of the skin by increasing the pressure of the one or more probe tips 106 against the tissue over a meridian point, to add moisture or water to the tissue where the measurement is taken, and/or to apply texture to the surface of the one or more probe tips 106 to help electricity flow through the insulation layer or a cornified layer of the tissue without puncturing.

It will be appreciated that the test subject needs to maintain a secure grip on the grounding device 102 to ensure the grounding area remains adequate throughout the testing cycle. To help reduce retesting and to ensure the test subject maintains a secure grip to the grounding device 102, a strap can be employed to ensure the hand to the grounding device 102 contact is secure. The grounding device 102 may include a texture applied to the grounding surface 104 that helps penetrate the insulation layer or cornified layer of the tissue without puncturing it. In an embodiment, the one or more processors 118 are configurable to execute instructions stored in non-transitory computer readable storage media. The instructions may include receiving a first bioelectrical measurement from the electrodermal sensor 110 and calculating a first conductivity value based on the first bioelectrical measurement. The instructions include receiving a second bioelectrical measurement from the electrodermal sensor 110 and calculating a second conductivity value based on the second bioelectrical measurement. The instructions include determining a standard conductivity value by retrieving the standard conductivity value from memory, receiving the standard conductivity value over a network, calculating the standard conductivity value based on a plurality of datapoints, and so forth. The instructions include calculating a compensation factor based on the standard conductivity value, the first conductivity value, and the second conductivity value.

The one or more processors 118 may use an algorithm or protocol to evaluate the test subject's unique skin conductivity, which is then compared to a pre-determined standard conductivity value, and then a compensation factor is generated to be applied to all measurements so that the test data being generated and graphed will be accurate. The measurement may be displayed on the screen 116. The algorithm or protocol tests the skin conductivity at one or more non-meridian locations to see if its resistance is in line with the 98,000 Ohms that the industry considers being normal. It would be preferred to test at multiple locations, for example at least three distinct non-meridian locations, to have enough data to establish an accurate compensation factor for the test subject.

The instructions executed by the one or more processors 118 may include averaging resistance measurements received from the electrodermal sensor 110 with normal tissue (around the 98,000 Ohm range) and adjusting the compensation factor accordingly. For example, if the subject being tested had a normal (non-meridian) skin resistance measurement of 94,000 ohms, then the system may apply a compensation factor or multiplier of (98,000/94,000) or about 1.043 to all of the initial ohm measurements before they are translated into a Voll conductivity factor or some other conductivity factor and input it into the predictive algorithm.

Figure 2:
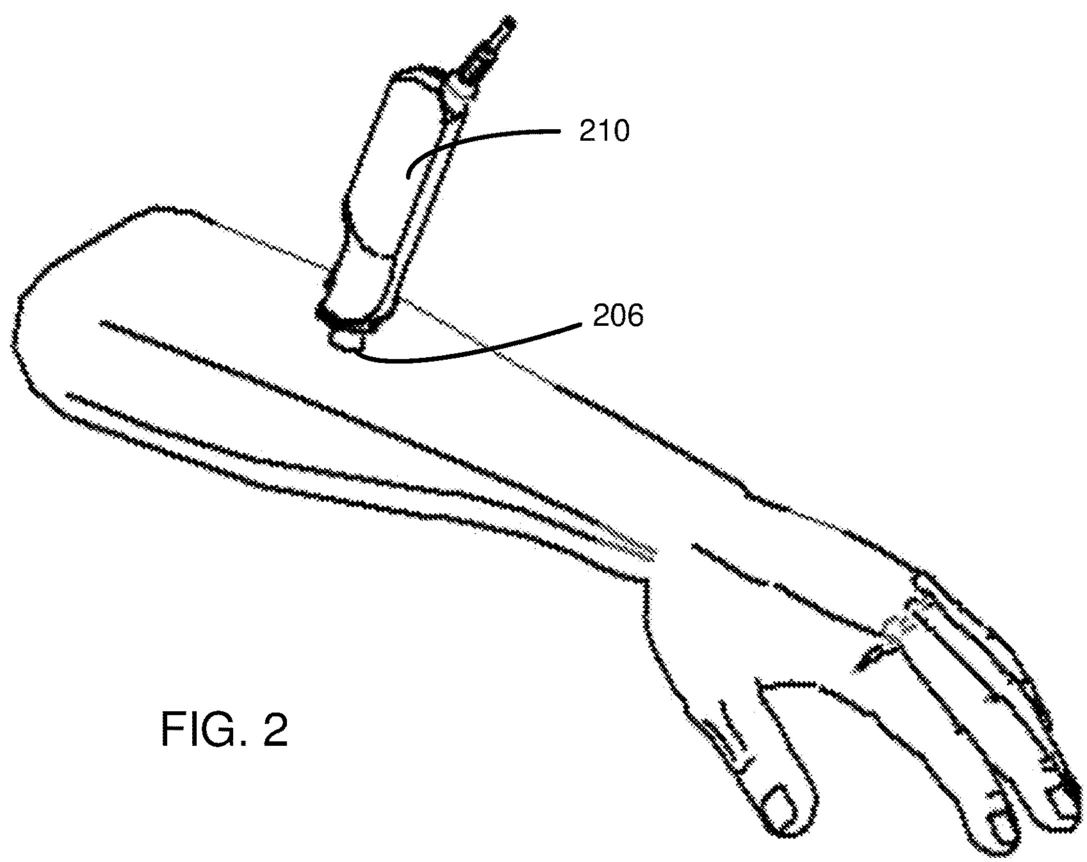
FIG. 2 illustrates an example of performing a bioelectric test at a non-meridian skin site of a user on the posterior side of the forearm of the user.
Figure 3:
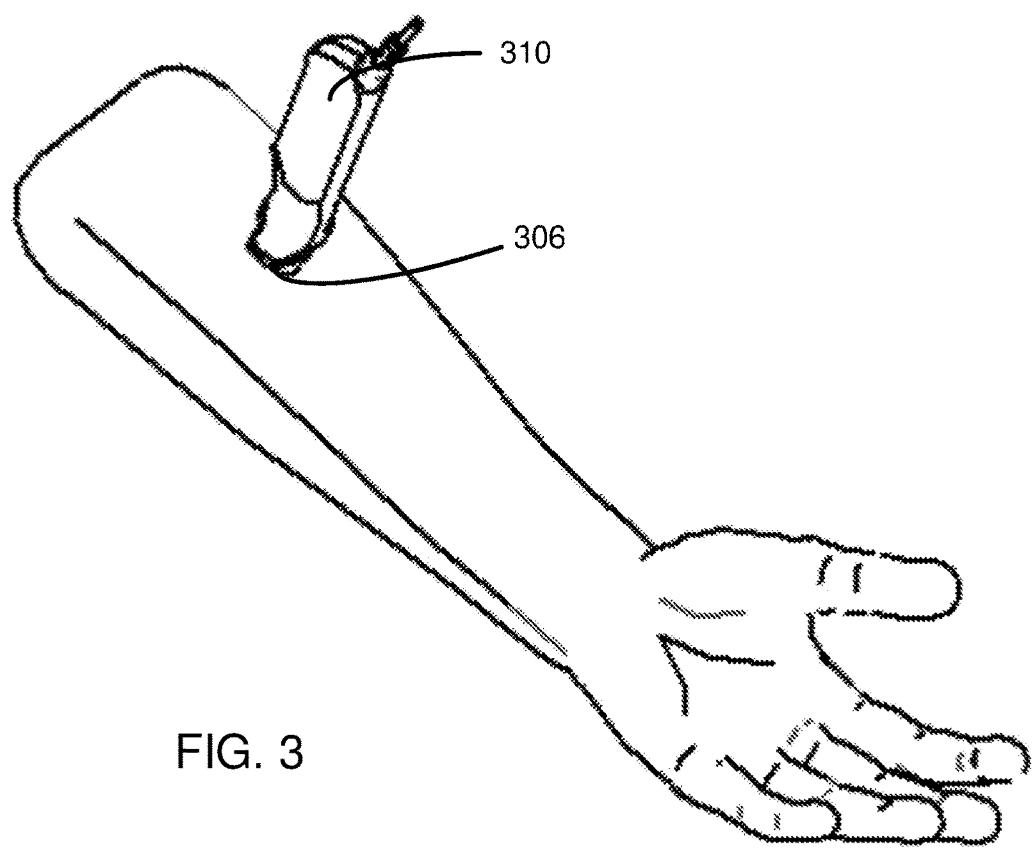
FIG. 3 illustrates an example of performing a bioelectric test at a non-meridian skin site of a user on the anterior side of the forearm of the user.
Figure 4:
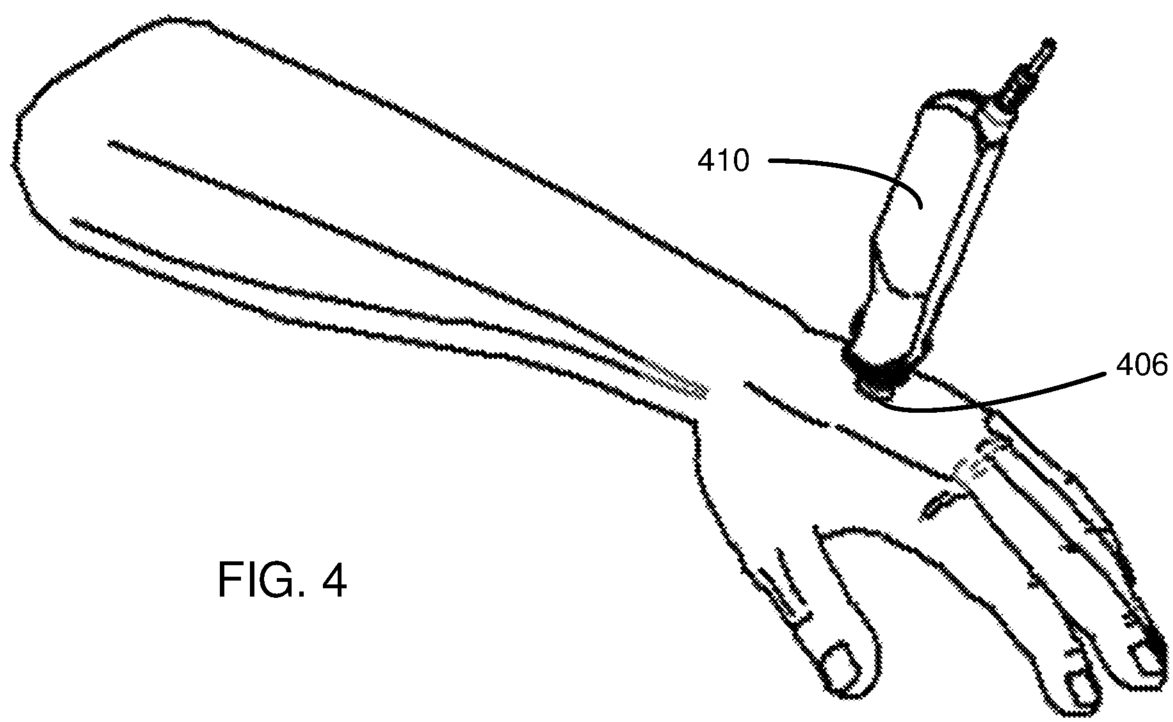
FIG. 4 illustrates an example of performing a bioelectric test at a non-meridian skin site of a user on the posterior side of the hand of the user.
Figure 5:
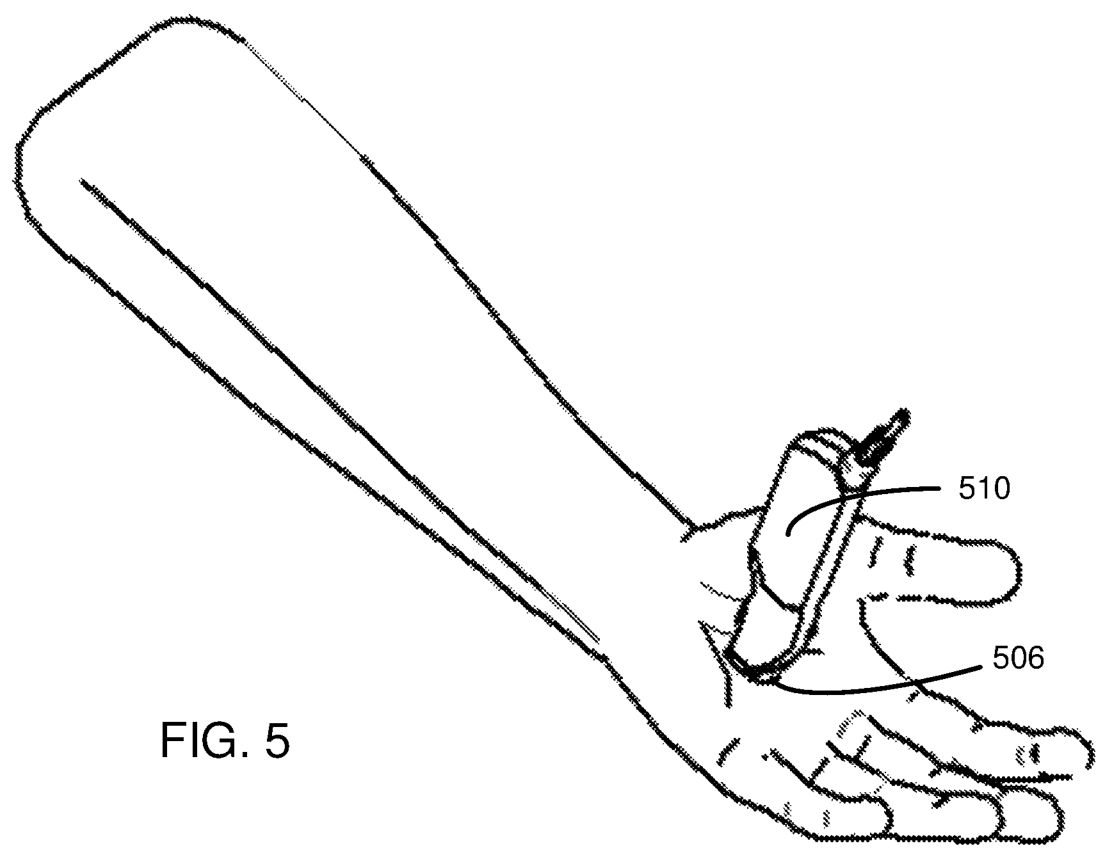
FIG. 5 illustrates an example of performing a bioelectric test at a non-meridian skin site of a user on the anterior side of the hand of the user within the user's palm.

FIGS. 2-5 illustrate examples of a bioelectric measurement being taking at different non-meridian skin sites of a user. FIG. 2 illustrates a bioelectric measurement being taken on a posterior side of the user's forearm. FIG. 3 illustrates a bioelectric measurement being taken on an anterior side of the user's forearm. FIG. 4 illustrates a bioelectric measurement being taken on a posterior side of the user's hand, opposite the user's palm. FIG. 5 illustrates a bioelectric measurement being taken on anterior side of the user's hand, within the user's palm. The non-meridian skin sites illustrated in FIGS. 2-5 are illustrative only and additional or different non-meridian skin sites may be tested for the purpose of calculating the compensation factor.

The skin resistance measurements are taken at non-meridian skin sites on the surface of the skin of the user. An electrodermal sensor 210, 310, 410, 510 is used to take the skin resistance measurements. The skin resistance measurements can easily be inversed to calculate a skin resistivity measurement. The electrodermal sensor 210, 310, 410, 510 includes one or more probe tips 206, 306, 406, 506 that are pressed against the skin at the non-meridian skin site for taking the skin resistance measurement.

The skin resistance measurements taken by the electrodermal sensor 210, 310, 410, 510 can be provided to the one or more processors 118 for further assessment. The one or more processors 118 may analyze the skin resistance measurements to determine a skin conductivity value for each of the non-meridian skin sites. The one or more processors 118 may average a plurality of skin resistance measurements to calculate a mean skin resistance measurement. The mean skin resistance measurement may be used to calculate a mean conductivity value for the user's skin. The one or more processors 118 may first convert the skin resistance measurements into skin conductivity values and may then average the skin conductivity values to calculate a mean skin conductivity value for the user's skin.

The one or more processors 118 may assess the mean skin conductivity value, the mean skin resistance measurement, and/or one or more of the skin conductivity values or one or more of the skin resistance measurements to calculate the compensation factor for the user's skin. The compensation factor is calculated by comparing the measured values for the user's skin against a standard conductivity value. The standard conductivity value is based on a plurality of measurements for a plurality of test subjects. The standard conductivity value may be stored in memory in the bioelectric measurement system 100, may be retrieved from a database, may be received over a network or other communication source, and so forth.

In an embodiment, a plurality of standard conductivity values are calculated, and the most applicable standard conductivity value is selected for comparison against non-meridian skin resistivity measurements for calculating the compensation factor for a user. A single standard conductivity value may be most applicable for a person of a certain gender, age, racial background, location of residence, and so forth. The location of residence may adjust the resistivity of a user's skin because a dryer climate may cause a user's skin to be dryer and therefore have a lower resistance value. Further, a more humid climate may cause a user's skin to be more hydrated and therefore have a greater resistance value. Additionally, skin resistivity measurements taken on a broad range of people indicate trends in skin resistivity based on the user's gender, age, racial background, and other factors. These factors may be associated with a standard skin conductivity value. In an embodiment, the standard skin conductivity value that is selected for comparison against a user's non-meridian skin resistivity measurements is selected based on similarity with the user with respect to pertinent factors such as age, gender, racial background, location of residence, and/or humidity at the test location.

In an embodiment, a plurality of standard skin conductivity values are stored in a database, a datastore, locally to the system 100, or elsewhere. The one or more processors 118 of the system 100 are configured to select a certain standard skin conductivity value based on a plurality of factors such as the user's age, gender, racial background, location of residence, and/or humidity at the test location. In another embodiment, the certain standard skin conductivity value is manually selected by a health practitioner operating the system 100 based on the user's age, gender, racial background, location of residence, and/or humidity at the test location. Each of the plurality of standard skin conductivity values may include metadata indicating the age, gender, racial background, location of residence, humidity at the test location, and/or other factors that are applicable to that standard skin conductivity value. Each of the plurality of standard skin conductivity values may be calculated based on skin resistivity measurements taken for numerous test subjects over time. The skin resistivity measurements for the numerous test subjects may be averaged or otherwise analyzed to calculate a standard skin conductivity value that may be referenced for future tests.

The certain standard skin conductivity value may further be selected based on where the non-meridian skin resistivity measurements are taken on the user. For example, thin non-calloused skin on a person's forearm has a lower resistivity (and therefore a higher conductivity) than tissue on the palm of a person's hand. The plurality of standard skin conductivity values may be associated with a certain location on a user's body or may be calculated based on a plurality of measurements over a plurality of skin sites.

In an embodiment, a standard skin conductivity value is 98,000 ohms. The standard skin conductivity value may vary based on gender, age, racial background, location of residence, humidity at the testing location, and other factors. Therefore, a plurality of skin conductivity values may be referenced and the standard skin conductivity value may be selected based on similarity with the test subject.

Figure 6A:
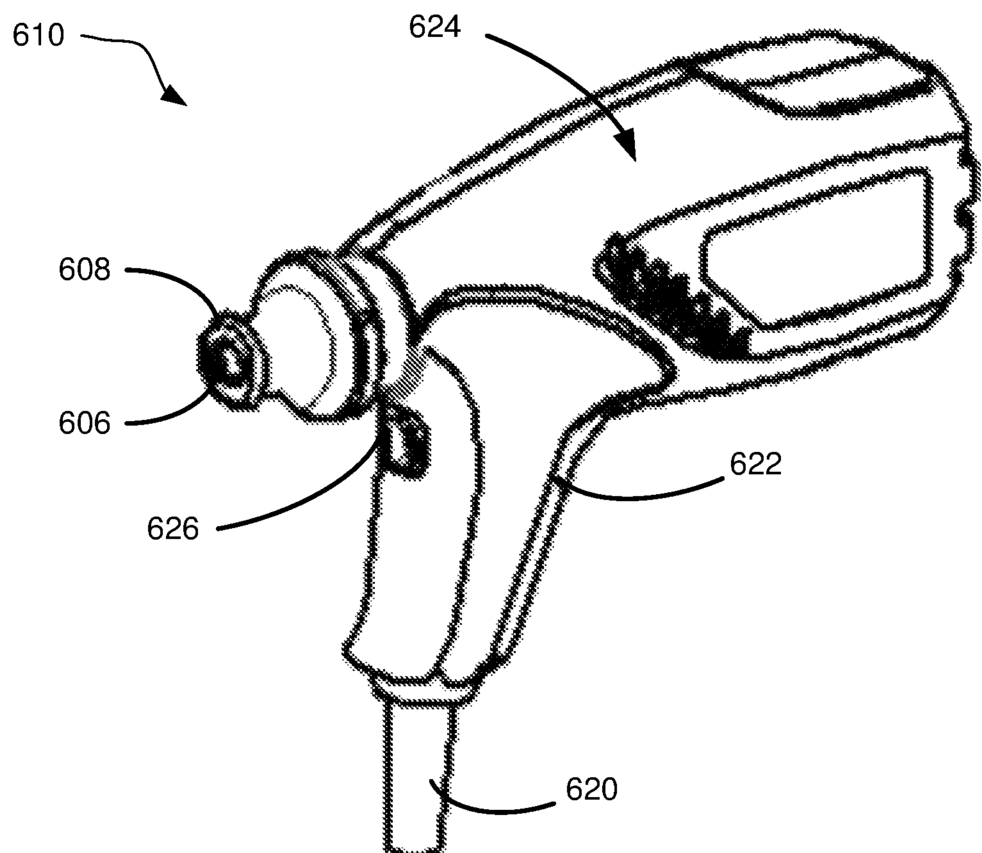
FIGS. 6A and 6B illustrate a perspective view of an electrodermal sensor.
Figure 6B:
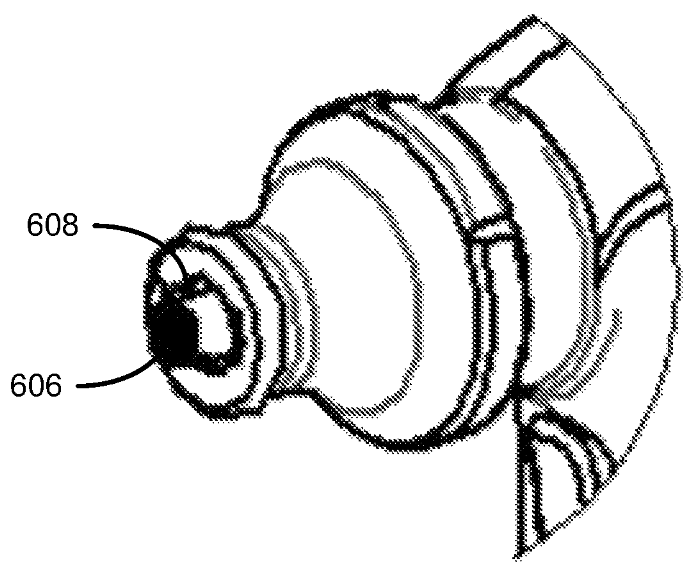

FIGS. 6A and 6B illustrate perspective views of an electrodermal sensor 610. FIG. 6A illustrates a pulled back perspective view of the electrodermal sensor 610 and FIG. 6B illustrates a detail perspective view of a portion of the electrodermal sensor 610 including the sensor hood and probe tips.

In an embodiment, the electrodermal sensor 610 includes a sensor hood 608. The sensor hood 608 may incorporate one or more grounding pads. The one or more grounding pads may be integrated into the sensor hood 608.

The electrodermal sensor 610 includes one or more probe tips 606 for taking resistance measurements of a material or tissue. Each of the one or more probe tips 606 may function independently and take an independent resistance measurement of the material or tissue. The one or more probe tips 606 are located at a distal end of the electrodermal sensor 610.

The electrodermal sensor 610 may further include a grip member 620 extending off the main body 624 of the electrodermal sensor 610 that is substantially perpendicular to the main body 624. The electrodermal sensor 610 may further include a trigger switch 626 for activating the electrodermal sensor 610 or causing the electrodermal sensor 610 to take a resistance measurement. The electrodermal sensor 610 may be powered by an external battery.

Figure 7:
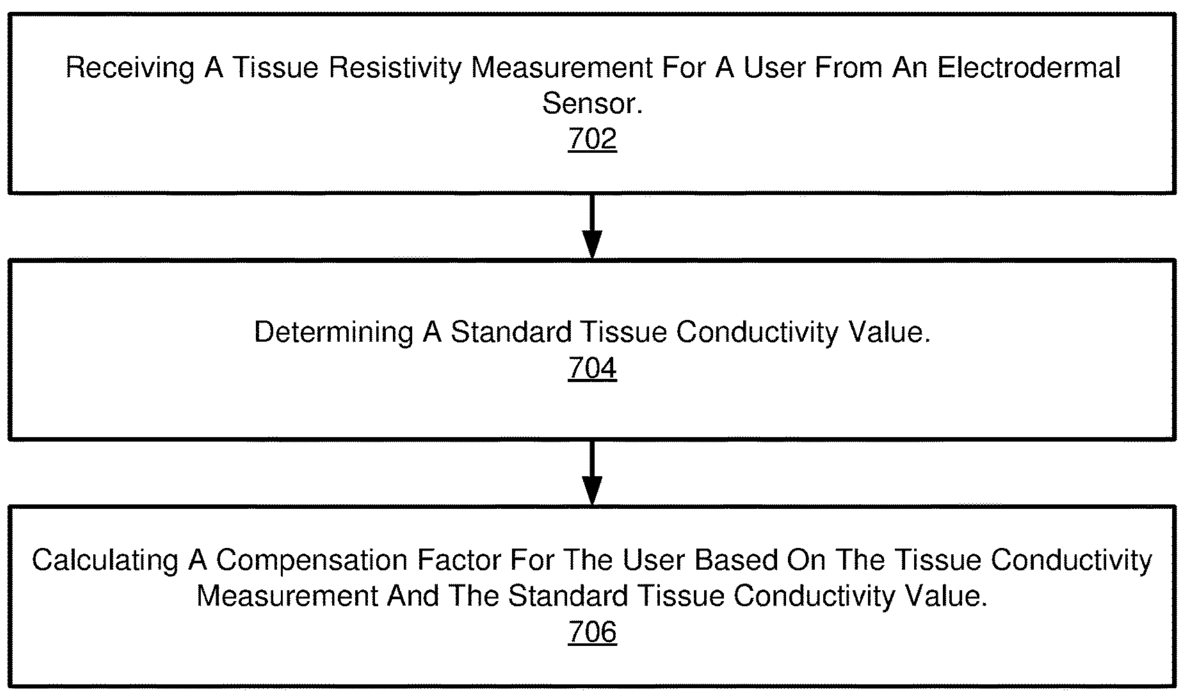
FIG. 7 illustrates a schematic flow chart diagram of a method for calculating a compensation factor for tissue conductivity.

FIG. 7 is a schematic flow chart diagram of a method 700 for calculating a compensation factor for tissue conductivity. The method 700 may be performed by any suitable computing device such as one or more processors 118 in electrical communication with an electrodermal sensor 110 and/or a ground device 102.

The method 700 begins and a computing device receives at 702 a tissue resistivity measurement for a user from an electrodermal sensor. Because resistance and conductivity are merely inverses of one another, the skin resistivity measurement may alternatively be referred to as a skin conductivity measurement. The method 700 continues and a computing device determines at 704 a standard tissue conductivity value. The standard tissue conductivity value may be for the same type of tissue as the tissue measured in step 702. For example, the tissue resistivity measurement received at 702 may be fore skin tissue, and the standard tissue conductivity value may also be for skin tissue. The determining the standard skin conductivity value at 704 may include retrieving the value from a database, receiving the value over a network or other communication pathway, retrieving the value from memory, and so forth. The method 700 continues and a computing device calculates at 706 a compensation factor for the user based on the tissue resistivity measurement and the standard tissue conductivity value.

Figure 8:
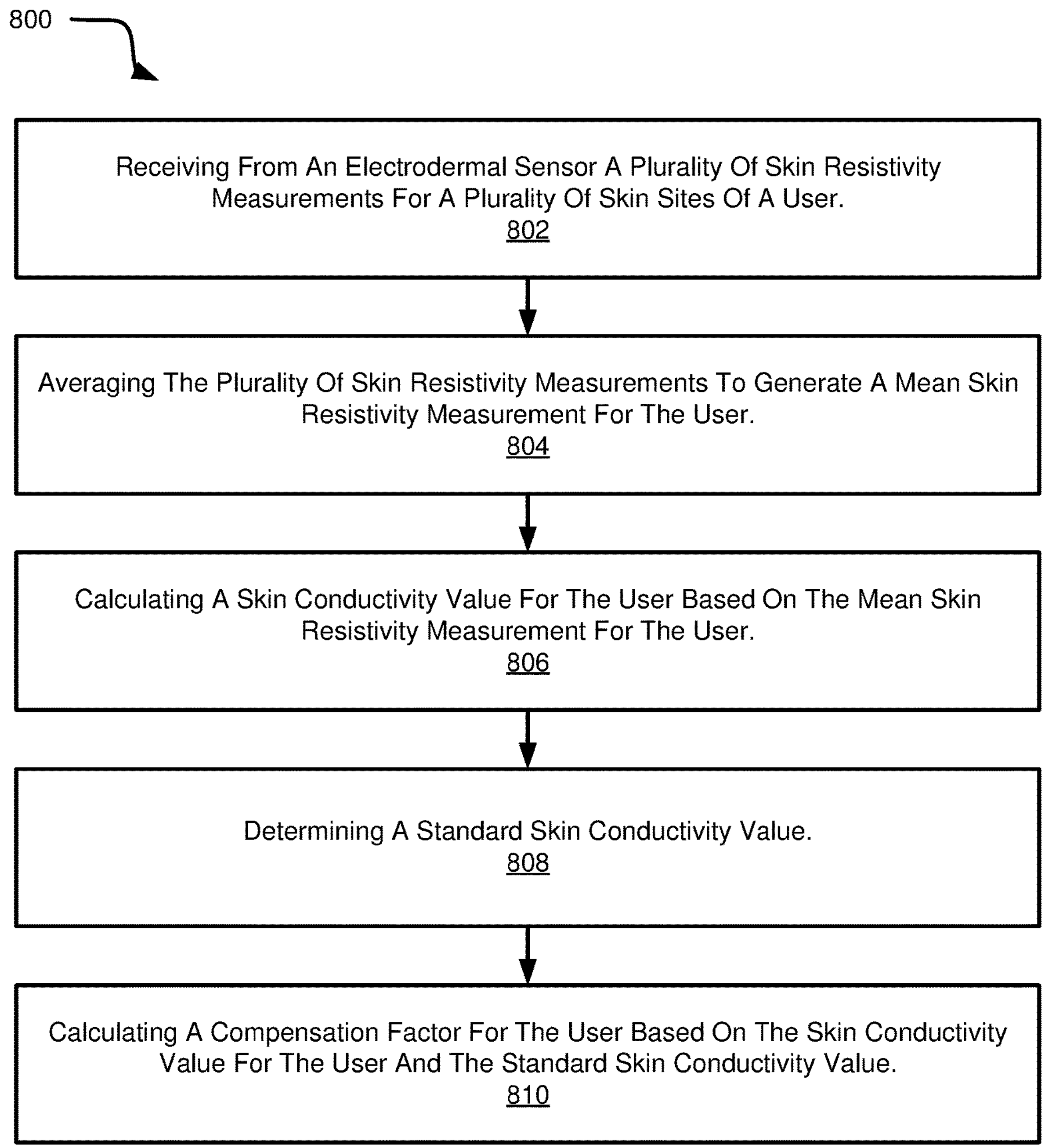
FIG. 8 illustrates a schematic flow chart diagram of a method for calculating a compensation factor for tissue conductivity.

FIG. 8 is a schematic flow chart diagram of a method 800 for calculating a compensation factor for tissue conductivity. The method 800 may be performed by any suitable computing device such as one or more processors 118 in electrical communication with an electrodermal sensor 110 and/or a ground device 102.

The method 800 begins and a computing device receives at 802 from an electrodermal sensor a plurality of skin resistivity measurements for a plurality of skin sites of a user. Because resistance and conductivity are merely inverses of one another, the skin resistivity measurement may alternatively be referred to as a skin conductivity measurement. A computing device averages at 804 the plurality of skin resistivity measurements to generate a mean skin resistivity measurement for the user. A computing device calculates at 806 a skin conductivity value for the user based on the mean skin resistivity measurement for the user. A computing device determines at 808 a standard skin conductivity value. A computing device calculates at 810 a compensation factor for the user based on the skin conductivity value for the user and the standard skin conductivity value.

FIG. 9 is a schematic flow chart diagram of a method 900 for calculating a compensation factor for tissue conductivity. The method 900 may be performed by any suitable computing device such as one or more processors 118 in electrical communication with an electrodermal sensor 110 and/or a ground device 102.

The method 900 begins and a computing device receives at 902 from an electrodermal sensor a plurality of skin resistivity measurements for a plurality of skin sites of a user. Because resistance and conductance are merely inverses of one another, the skin resistivity measurement may alternatively be referred to as a skin conductivity measurement. A computing device calculates at 904 a plurality of skin conductivity values for the user based on the plurality of skin resistivity measurements. A computing device averages at 906 the plurality of skin conductivity values for the user to calculate a mean skin conductivity value for the user. A computing device determines at 908 a standard skin conductivity value. A computing device calculates at 910 a compensation factor for the user based on the mean skin conductivity value for the user and the standard skin conductivity value.

FIG. 10 is a schematic flow chart diagram of a method 1000 for calculating a compensation factor for tissue conductivity. The method 1000 may be performed by any suitable computing device such as one or more processors 118 in electrical communication with an electrodermal sensor 110 and/or a ground device 102.

The method 1000 begins and a computing device receives at 1002 from an electrodermal sensor a skin resistivity measurement for a non-meridian skin site on a user. Because resistance and conductance are mere inverses of one another, the skin resistivity measurement may alternatively be referred to as a skin conductivity measurement. A computing device determines at 1004 a standard skin conductivity value. A computing device calculates at 1006 a compensation factor for the user based on the skin resistivity measurement and the standard skin conductivity value. A computing device receives at 1008 from the electrodermal sensor a meridian resistivity measurement for a meridian pathway of the user. A computing device calculates at 1010 a conductivity value for the user based at least in part on the compensation factor and the meridian resistivity measurement.

In an embodiment, the compensation factor is calculated further based on one or more of the age, gender, racial background, location of residence, or humidity at the testing location for the user. These values may be ascertained and computed in the compensation factor. In an embodiment, the standard skin conductivity value is selected based on similarity with the test subject with respect to one or more of age, gender, racial background, location of residence, or humidity at the testing location.

Figure 11:
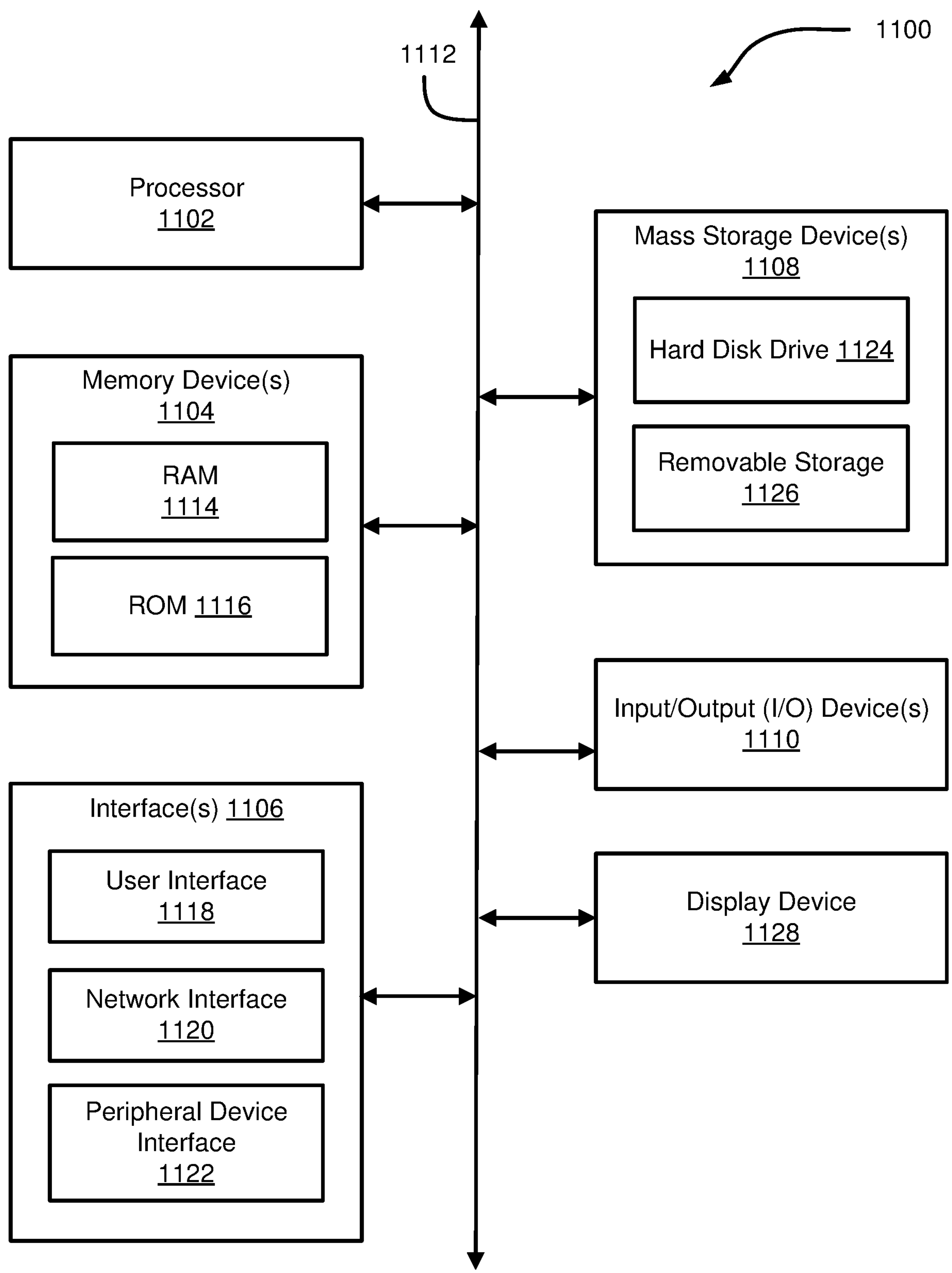
FIG. 11 is a block diagram of an example computing device in accordance with the teachings and principles of the disclosure.

FIG. 11 is a block diagram illustrating an example computing device 1100. Computing device 1100 may be used to perform various procedures, such as those discussed herein. Computing device 1100 can function as a server, a client, or any other computing entity such as the one or more processors 118 in communication with the electrodermal sensor 110 and/or the grounding device 102. Computing device can perform various monitoring functions as discussed herein, and can execute one or more application programs, such as the application programs described herein. Computing device 1100 can be any of a wide variety of computing devices, such as a desktop computer, a notebook computer, a server computer, a handheld computer, tablet computer and the like.

Computing device 1100 may include one or more processor(s) 1102, one or more memory device(s) 1104, one or more interface(s) 1106, one or more mass storage device(s) 1108, one or more Input/Output (I/O) device(s) 1110, and a display device 1128 all of which are coupled to a bus 112. Processor(s) 1102 include one or more processors or controllers that execute instructions stored in memory device(s) 1104 and/or mass storage device(s) 1108. Processor(s) 1102 may also include various types of computer-readable media, such as cache memory.

Memory device(s) 1104 include various computer-readable media, such as volatile memory (e.g., random access memory (RAM) 1114) and/or nonvolatile memory (e.g., read-only memory (ROM) 1116). Memory device(s) 1104 may also include rewritable ROM, such as Flash memory.

Mass storage device(s) 1108 include various computer readable media, such as magnetic tapes, magnetic disks, optical disks, solid-state memory (e.g., Flash memory), and so forth. As shown in FIG. 11, a particular mass storage device is a hard disk drive 1124. Various drives may also be included in mass storage device(s) 1108 to enable measurement from and/or writing to the various computer readable media. Mass storage device(s) 1108 include removable media 1126 and/or non-removable media.

I/O device(s) 1110 include various devices that allow data and/or other information to be input to or retrieved from computing device 1100. Example I/O device(s) 1110 include cursor control devices, keyboards, keypads, microphones, monitors or other display devices, speakers, printers, network interface cards, modems, lenses, CCDs or other image capture devices, and the like.

Display device 1128 includes any type of device capable of displaying information to one or more users of computing device 1100. Examples of display device 112 include a monitor, display terminal, video projection device, and the like.

Interface(s) 1106 include various interfaces that allow computing device 1100 to interact with other systems, devices, or computing environments. Example interface(s) 1106 may include any number of different network interfaces 1120, such as interfaces to local area networks (LANs), wide area networks (WANs), wireless networks, and the Internet. Other interface(s) include user interface 1118 and peripheral device interface 1122. The interface(s) 1106 may also include one or more user interface elements 1118. The interface(s) 1106 may also include one or more peripheral interfaces such as interfaces for printers, pointing devices (mice, track pad, or any suitable user interface now known to those of ordinary skill in the field, or later discovered), keyboards, and the like.

Bus 1112 allows processor(s) 1102, memory device(s) 1104, interface(s) 1106, mass storage device(s) 1108, and I/O device(s) 1110 to communicate with one another, as well as other devices or components coupled to bus 1112. Bus 1112 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1100, and are executed by processor(s) 1102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Implementations of the disclosure may comprise or utilize a special purpose or general-purpose computer including computer hardware, such as, for example, one or more processors and system memory, as discussed in greater detail below. Implementations within the scope of the disclosure also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media devices or vice versa. For example, computer-executable instructions or data structures received over a network or data link can be buffered in RAM 1114 within a network interface module 1120 (e.g., a "NIC"), and then eventually transferred to computer system RAM 1114 and/or to less volatile computer storage media (devices) at a computer system. RAM 1114 can also include solid state drives (SSDs or PCIx based real time memory tiered storage, such as FusionIO). Thus, it should be understood that computer storage media devices can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the disclosure can also be used in cloud computing environments. In this description and the following claims, "cloud computing" is defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, or any suitable characteristic now known to those of ordinary skill in the field, or later discovered), service models (e.g., Software as a Service (SaaS), Platform as a Service (PaaS), Infrastructure as a Service (IaaS)), and deployment models (e.g., private cloud, community cloud, public cloud, hybrid cloud, or any suitable service type model now known to those of ordinary skill in the field, or later discovered). Databases and servers described with respect to the disclosure can be included in a cloud model.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

EXAMPLES

The following examples pertain to further embodiments.

Example 1 is a system including an electrodermal sensor and one or more processors in electrical communication with the electrodermal sensor and configurable to execute instructions stored in non-transitory computer readable storage media. The instructions include receiving a skin resistance measurement for a user from the electrodermal sensor, determining a standard skin conductivity value, and calculating a compensation factor for the user based on the skin resistance measurement and the standard skin conductivity value.

Example 2 is a system as in Example 1, wherein receiving the skin resistance measurement for the user comprises receiving a plurality of skin resistance measurements from a plurality of skin sites on the user, and wherein the instructions further comprise averaging the plurality of skin resistance measurements to calculate a mean skin conductivity value for the user.

Example 3 is a system as in any of Examples 1-2, wherein calculating the compensation factor for the user comprises calculating based on the standard skin conductivity value and the mean skin conductivity value for the user.

Example 4 is a system as in any of Examples 1-3, further comprising a grounding device in electrical communication with the one or more processors and configured to ground the user for capturing the skin resistance measurement.

Example 5 is a system as in any of Examples 1-4, wherein the electrodermal sensor comprises a plurality of probe tips for sensing resistivity of tissue, wherein each of the plurality of probe tips is independent and makes an independent measurement of resistivity of a tissue.

Example 6 is a system as in any of Examples 1-5, wherein the instructions further comprise averaging independent measurements for resistivity of the skin of the user from each of the plurality of probe tips.

Example 7 is a system as in any of Examples 1-6, further comprising a display in electrical communication with the one or more processors and configured to display the compensation factor.

Example 8 is a system as in any of Examples 1-7, wherein the electrodermal sensor further comprises a sensor hood and a grounding pad disposed within the sensor hood.

Example 9 is a system as in any of Examples 1-8, wherein the instructions are such that: receiving the skin resistance measurement for the user comprises receiving a measurement for a non-meridian skin site on the user; and determining the standard skin conductivity value comprises retrieving from memory a predefined conductivity value for a non-meridian skin site.

Example 10 is a system as in any of Examples 1-9, wherein the instructions further comprise: receiving from the electrodermal sensor a meridian resistivity measurement for a meridian pathway of the user; and calculating a conductivity value for the user based at least in part on the compensation factor and the meridian resistivity measurement.

Example 11 is a method. The method includes receiving a skin resistance measurement for a skin site of a user from an electrodermal sensor. The method includes determining a standard skin conductivity value. The method includes calculating a compensation factor for the user based on the skin resistance measurement and the standard skin conductivity value.

Example 12 is a method as in Example 11, wherein receiving the skin resistance measurement for the user comprises receiving a plurality of skin resistance measurements from a plurality of skin sites on the user, and wherein the instructions further comprise averaging the plurality of skin resistance measurements to calculate a mean skin conductivity value for the user.

Example 13 is a method as in any of Examples 11-12, wherein calculating the compensation factor for the user comprises calculating based on the standard skin conductivity value and the mean skin conductivity value for the user.

Example 14 is a method as in any of Examples 11-13, further comprising: receiving a plurality of independent skin resistance measurements for the skin site of the user captured by a plurality of probe tips of the electrodermal sensor; and averaging the plurality of independent skin resistance measurements to calculate a mean skin resistance measurement for the skin site; wherein calculating the compensation factor for the user comprises calculating based at least in part on the mean skin resistance measurement for the skin site and the standard skin conductivity value.

Example 15 is a method as in any of Examples 11-14, further comprising: receiving from the electrodermal sensor a meridian resistivity measurement for a meridian pathway of the user; and calculating a conductivity value for the user based at least in part on the compensation factor and the meridian resistivity measurement.

Example 16 is non-transitory computer readable storage media storing instructions to be executed by one or more processors, the instructions comprising: receiving a skin resistance measurement for a skin site of a user from an electrodermal sensor; determining a standard skin conductivity value; and calculating a compensation factor for the user based on the skin resistance measurement and the standard skin conductivity value.

Example 17 is non-transitory computer readable storage media as in Example 16, wherein the instructions are such that: receiving the skin resistance measurement for the user comprises receiving a measurement for a non-meridian skin site on the user; and determining the standard skin conductivity value comprises retrieving from memory a predefined conductivity value for a non-meridian skin site.

Example 18 is non-transitory computer readable storage media as in any of Examples 16-, wherein the instructions further comprise: receiving from the electrodermal sensor a meridian resistivity measurement for a meridian pathway of the user; and calculating a conductivity value for the user based at least in part on the compensation factor and the meridian resistivity measurement.

Example 19 is non-transitory computer readable storage media as in any of Examples 16-18, wherein: receiving the skin resistance measurement for the user comprises receiving a plurality of skin resistance measurements from a plurality of skin sites on the user; the instructions further comprise averaging the plurality of skin resistance measurements to calculate a mean skin conductivity value for the user; and calculating the compensation factor for the user comprises calculating based on the standard skin conductivity value and the mean skin conductivity value for the user.

Example 20 is non-transitory computer readable storage media as in any of Examples 16-19, wherein the instructions further comprise: receiving a plurality of independent skin resistance measurements for the skin site of the user captured by a plurality of independent test probes of the electrodermal sensor; and averaging the plurality of independent skin resistance measurements to calculate a mean skin resistance measurement for the skin site; wherein calculating the compensation factor for the user comprises calculating based at least in part on the mean skin resistance measurement for the skin site and the standard skin conductivity value.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:

an electrodermal sensor that applies a direct current and measures electrical resistance in response to application of the direct current;

a grounding device comprising a handheld mass to be held by a user that grounds the user when the electrodermal sensor applies the direct current; and a processor configurable to execute instructions stored in non-transitory computer readable storage media, the instructions comprising:

determining a non-meridian skin resistance for the user, wherein the non-meridian skin resistance is sensed by the electrodermal sensor;

determining a standard skin conductivity value, wherein the standard skin conductivity value is calculated based on skin conductivity values for a plurality of test subjects;

calculating a compensation factor for the user based on the non-meridian skin resistance and the standard skin conductivity value; and applying the compensation factor to meridian conductivity measurements for the user to adjust for abnormal skin conductivity of the user.

2. The system of claim 1, wherein determining the non-meridian skin resistance for the user comprises receiving a plurality of non-meridian skin resistance measurements from a plurality of skin sites on the user, and wherein the instructions further comprise averaging the plurality of non-meridian skin resistance measurements to calculate a mean skin conductivity value for the user.

3. The system of claim 2, wherein calculating the compensation factor for the user comprises dividing the standard skin conductivity value by the mean skin conductivity value for the user.

4. The system of claim 1, wherein the handheld mass of the grounding device is held by the user when the direct current is applied to the user's skin.

5. The system of claim 1, wherein the electrodermal sensor comprises a plurality of probe tips for sensing resistivity of tissue, and wherein each of the plurality of probe tips is independent and senses an independent measurement of resistivity of a tissue.

6. The system of claim 5, wherein the instructions further comprise averaging independent measurements for resistivity of the skin of the user from each of the plurality of probe tips.

7. The system of claim 1, further comprising a display in electrical communication with the processor and configured to display the compensation factor.

8. The system of claim 1, wherein the electrodermal sensor further comprises a sensor hood and a grounding pad disposed within the sensor hood.

9. The system of claim 1, wherein the instructions are such that determining the standard skin conductivity value comprises retrieving from memory a certain standard skin conductivity value that is predetermined based on test subjects with similarity to the user with respect to one or more of age, gender, racial background, or location of residence.

10. The system of claim 1, wherein the instructions further comprise:

receiving from the electrodermal sensor a meridian conductivity measurement for a meridian pathway of the user;

applying the compensation factor to the meridian conductivity measurement; and calculating a conductivity value for the user based at least in part on the compensation factor and the meridian conductivity measurement.

11. A method comprising:

applying an electrodermal sensor to a non-meridian point on a user, wherein the electrodermal sensor supplies a direct current and measures electrical resistance in response to application of the direct current;

providing a grounding device to the user, wherein the grounding device comprises a mass to be held by the user to electrically ground the user when the electrodermal sensor supplies the direct current to the non-meridian point on the user;

receiving a non-meridian skin resistance for the user from the electrodermal sensor;

determining a standard skin conductivity value, wherein the standard skin conductivity value is calculated based on skin conductivity values for a plurality of test subjects;

calculating a compensation factor for the user based on the non-meridian skin resistance and the standard skin conductivity value;

applying the electrodermal sensor to a meridian point on the user to sense a meridian conductivity measurement of the user; and compensating for abnormal skin resistivity of the user by applying the compensation factor to the meridian conductivity measurement.

12. The method of claim 11, wherein receiving the non-meridian skin resistance for the user comprises receiving a plurality of skin resistance measurements from a plurality of skin sites on the user, and wherein the method further comprises averaging the plurality of skin resistance measurements to calculate a mean skin conductivity value for the user.

13. The method of claim 12, wherein calculating the compensation factor for the user comprises dividing the standard skin conductivity value by the mean skin conductivity value for the user.

14. The method of claim 11, further comprising:

applying the electrodermal sensor to the non-meridian point on the user to sense a plurality of independent skin resistance measurements for the non-meridian point with a plurality of probe tips of the electrodermal sensor; and averaging the plurality of independent skin resistance measurements to calculate a mean skin resistance measurement for the skin site;

wherein calculating the compensation factor for the user comprises dividing the standard skin conductivity value by the mean skin resistance measurement for the skin site.

15. The method of claim 11, further comprising calculating a conductivity value for the user based at least in part on the compensation factor and the meridian conductivity measurement.

16. Non-transitory computer readable storage media storing instructions to be executed by one or more processors, the instructions comprising:

causing an electrodermal sensor to supply a direct current and measure electrical resistance in response to application of the direct current;

receiving a non-meridian skin resistance for a user from the electrodermal sensor in response to the electrodermal sensor supplying the direct current to a non-meridian skin site on the user;

determining a standard skin conductivity value, wherein the standard skin conductivity value is calculated based on skin conductivity values for a plurality of test subjects;

calculating a compensation factor for the user based on the non-meridian skin resistance and the standard skin conductivity value;

causing the electrodermal sensor to supply the direct current to measure a meridian conductivity measurement of the user when the electrodermal sensor is applied to a meridian point on the user; and compensating for abnormal skin resistivity of the user by applying the compensation factor to the meridian conductivity measurement.

17. The non-transitory computer readable storage media of claim 16, wherein the instructions are such that determining the standard skin conductivity value comprises retrieving from memory a certain standard skin conductivity value that is predetermined based on test subjects with similarity to the user with respect to one or more of age, gender, racial background, or location of residence.

18. The non-transitory computer readable storage media of claim 16, wherein the instructions further comprise:

receiving from the electrodermal sensor the meridian conductivity measurement for a meridian pathway of the user; and calculating a conductivity value for the user based at least in part on the compensation factor and the meridian conductivity measurement.

19. The non-transitory computer readable storage media of claim 16, wherein:

the instructions are such that receiving the non-meridian skin resistance for the user comprises receiving a plurality of skin resistance measurements from a plurality of non-meridian skin sites on the user;

the instructions further comprise averaging the plurality of skin resistance measurements to calculate a mean skin conductivity value for the user; and the instructions are such that calculating the compensation factor for the user comprises dividing the standard skin conductivity value by the mean skin conductivity value for the user.

20. The non-transitory computer readable storage media of claim 16, wherein the instructions further comprise:

receiving a plurality of independent non-meridian skin resistance measurements for the non-meridian skin site of the user captured by a plurality of independent test probes of the electrodermal sensor; and averaging the plurality of independent non-meridian skin resistance measurements to calculate a mean skin resistance measurement for the non-meridian skin site;

wherein the instructions are such that calculating the compensation factor for the user comprises dividing the standard skin conductivity value by the mean skin resistance measurement for the non-meridian skin site.

* * * * *